(12) United States Patent
Yang et al.

(10) Patent No.: US 10,454,062 B2
(45) Date of Patent: *Oct. 22, 2019

(54) FUNCTIONAL MATERIAL, ITS PREPARATION METHOD, AND ORGANIC LIGHT EMITTING DIODE DISPLAY PANEL

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Jiuxia Yang, Beijing (CN); Feng Bai, Beijing (CN); Zhenpeng Guo, Beijing (CN); Jing Su, Beijing (CN); Jiantao Liu, Beijing (CN); Hongbo Feng, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 69 days.

This patent is subject to a terminal disclaimer.

(21) Appl. No.: 14/769,339

(22) PCT Filed: Nov. 21, 2014

(86) PCT No.: PCT/CN2014/091835
§ 371 (c)(1),
(2) Date: Aug. 20, 2015

(87) PCT Pub. No.: WO2016/015408
PCT Pub. Date: Feb. 4, 2016

(65) Prior Publication Data
US 2016/0254486 A1    Sep. 1, 2016

(30) Foreign Application Priority Data

Jul. 29, 2014  (CN) .......................... 2014 1 0367033

(51) Int. Cl.
*H01L 51/00* (2006.01)
*H01L 51/52* (2006.01)
(Continued)

(52) U.S. Cl.
CPC ........ *H01L 51/5253* (2013.01); *A61N 5/0613* (2013.01); *A61N 5/0625* (2013.01);
(Continued)

(58) Field of Classification Search
CPC ... C08K 9/08; C08K 3/38; C08K 3/22; C08K 2003/2203; C08K 2003/2244;
(Continued)

(56) References Cited

U.S. PATENT DOCUMENTS 3,863,325 A     2/1975  Gurganus et al.
4,487,911 A  *  12/1984 Lange ................ C08G 73/1028
                                                428/458
(Continued)

FOREIGN PATENT DOCUMENTS

CN    1656148 A    8/2005
CN    1718614 A    1/2006
(Continued)

OTHER PUBLICATIONS

ECR Glassflake (Glass Flake Limited) 2015.*
(Continued)

*Primary Examiner* — John D Freeman

(57) ABSTRACT

The present invention provides a functional material, its preparation method, and an organic light emitting diode display panel, which belongs to the display technical field and can solve the pollution problem in current organic light emitting diode display panels. The functional material comprises an inorganic mixed powder with a modified layer, the inorganic mixed powder comprising boron oxide, sodium oxide, lithium oxide, zirconium oxide, aluminum oxide, zinc (Continued)

oxide, titanium oxide, silicon dioxide, calcium oxide, silver complexes, silver phosphate, silver nitrate, tourmaline, silver thiosulfate, carbon nanotubes, aluminum sulfate, manganese, manganese oxide, iron, iron oxide, cobalt, cobalt oxide, nickel, nickel oxide, chromium, chromium oxide, copper, copper oxide, magnesium oxide, boron carbide, silicon carbide, titanium carbide, zirconium carbide, tantalum carbide, molybdenum carbide, boron nitride, chromium nitride, titanium nitride, zirconium nitride, aluminum nitride, chromium boride, $Cr_3B_4$, titanium boride, zirconium boride, tungsten disilicide, titanium disilicide and the like; the modified layer being generated by a reaction of a dianhydride and a diamine.

7 Claims, 2 Drawing Sheets

(51) Int. Cl.
| | |
|---|---|
| *A61N 5/06* | (2006.01) |
| *C09K 11/02* | (2006.01) |
| *C08K 9/08* | (2006.01) |
| *C09K 11/67* | (2006.01) |
| *C08K 3/22* | (2006.01) |
| *C08K 3/38* | (2006.01) |

(52) U.S. Cl.
CPC .......... *C09K 11/025* (2013.01); *C09K 11/676* (2013.01); *H01L 51/5262* (2013.01); *A61N 2005/066* (2013.01); *A61N 2005/0653* (2013.01); *C08K 3/22* (2013.01); *C08K 3/38* (2013.01); *C08K 9/08* (2013.01); *C08K 2003/2203* (2013.01); *C08K 2003/2244* (2013.01); *H01L 51/0053* (2013.01); *H01L 2251/303* (2013.01); *H01L 2251/5369* (2013.01); *H01L 2251/558* (2013.01); *Y10T 428/2998* (2015.01); *Y10T 428/31721* (2015.04)

(58) Field of Classification Search
CPC ...... Y10T 428/2998; Y10T 428/31721; A61N 2005/0653; A61N 2005/066; A61N 5/0613; A61N 5/0625; C09K 11/025; C09K 11/676; H01L 2251/303; H01L 2251/5369; H01L 2251/558; H01L 51/0053; H01L 51/5253; H01L 51/5262
See application file for complete search history.

(56) References Cited

U.S. PATENT DOCUMENTS

| | | | |
|---|---|---|---|
| 4,759,987 A | 7/1988 | Mizobe et al. | |
| 4,859,530 A * | 8/1989 | Roark | B32B 27/04 442/23 |
| 4,879,182 A | 11/1989 | Presswood et al. | |
| 4,996,293 A | 2/1991 | Tsuyoshi | |
| 5,344,916 A | 9/1994 | Harris et al. | |
| 5,367,012 A | 11/1994 | Aitken et al. | |
| 5,693,379 A | 12/1997 | Sugimori et al. | |
| 5,728,473 A * | 3/1998 | Inoue | B32B 7/12 428/448 |
| 6,540,825 B1 | 4/2003 | Quinn et al. | |
| 9,541,764 B2* | 1/2017 | Yang | G02B 27/22 |
| 9,587,121 B2* | 3/2017 | Yang | C09D 7/62 |
| 9,690,035 B2* | 6/2017 | Yang | C09C 3/10 |
| 9,796,928 B2* | 10/2017 | Yang | C09C 3/10 |
| 9,896,600 B2* | 2/2018 | Yang | C09C 1/40 |
| 10,007,031 B2* | 6/2018 | Yang | G02B 1/14 |
| 10,119,069 B2* | 11/2018 | Yang | C09K 11/025 |
| 2003/0013838 A1 | 1/2003 | Yamashita et al. | |
| 2003/0181626 A1 | 9/2003 | Lindway | |
| 2004/0220339 A1 | 11/2004 | Chen et al. | |
| 2005/0170180 A1 | 8/2005 | Kawa | |
| 2006/0003173 A1* | 1/2006 | Usuki | B32B 7/12 428/458 |
| 2006/0240232 A1 | 10/2006 | Faris | |
| 2007/0154716 A1 | 7/2007 | Czubarow et al. | |
| 2007/0231588 A1 | 10/2007 | Kanakarajan et al. | |
| 2007/0242055 A1 | 10/2007 | Lai | |
| 2008/0066802 A1 | 3/2008 | Reddy | |
| 2009/0197068 A1 | 8/2009 | Yamaguchi et al. | |
| 2010/0003507 A1 | 1/2010 | Wu et al. | |
| 2010/0270919 A1* | 10/2010 | Hubert | H01L 51/5246 313/512 |
| 2011/0123722 A1 | 5/2011 | Yang et al. | |
| 2012/0181914 A1* | 7/2012 | Fukuda | B32B 15/08 313/46 |
| 2013/0012643 A1* | 1/2013 | Monsheimer | B29C 67/04 524/494 |
| 2013/0037786 A1 | 2/2013 | Miyao et al. | |
| 2013/0146346 A1 | 6/2013 | Nakamoto et al. | |
| 2013/0150523 A1 | 6/2013 | Xiao et al. | |
| 2013/0158195 A1 | 6/2013 | Chen et al. | |
| 2013/0164466 A1* | 6/2013 | Khadilkar | C09D 5/34 428/34.5 |
| 2014/0091294 A1 | 4/2014 | Chen et al. | |
| 2014/0184997 A1 | 7/2014 | Yan et al. | |
| 2014/0220335 A1 | 8/2014 | Lin et al. | |
| 2014/0252386 A1 | 9/2014 | Ito et al. | |
| 2015/0331315 A1 | 11/2015 | Yang et al. | |

FOREIGN PATENT DOCUMENTS

| | | | |
|---|---|---|---|
| CN | 100999589 A | 7/2007 | |
| CN | 101225208 A | 7/2008 | |
| CN | 101260235 A | 9/2008 | |
| CN | 101343425 A | 1/2009 | |
| CN | 101426338 A | 5/2009 | |
| CN | 101805517 A | 8/2010 | |
| CN | 102039100 A | 5/2011 | |
| CN | 102079899 A | 6/2011 | |
| CN | 102634020 A | 8/2012 | |
| CN | 102643424 A | 8/2012 | |
| CN | 102707496 A | 10/2012 | |
| CN | 102707503 A | 10/2012 | |
| CN | 102898833 A | 1/2013 | |
| CN | 103059298 A | 4/2013 | |
| CN | 103102075 A | 5/2013 | |
| CN | 103160123 A | 6/2013 | |
| CN | 103232609 A | 8/2013 | |
| CN | 103555003 A | 2/2014 | |
| CN | 103739205 A | 4/2014 | |
| EP | 0646632 A1 | 4/1995 | |
| EP | 1387367 B1 | 2/2004 | |
| EP | 1912084 A1 | 4/2008 | |
| JP | 05-051541 A | 3/1993 | |
| JP | 05051541 A | 3/1993 | |
| JP | 2001-139345 A | 5/2001 | |
| JP | 2002-285031 A | 10/2002 | |
| JP | 2004-341380 A | 12/2004 | |
| JP | 2004-341381 A | 12/2004 | |
| JP | 2005-029584 A | 2/2005 | |
| JP | 2005-231934 A | 9/2005 | |
| JP | 2007-254523 A | 10/2007 | |
| JP | 2011-222333 A | 11/2011 | |
| KR | 20050087483 A | 8/2005 | |
| TW | 201002761 A | 1/2010 | |
| WO | 2004/023511 A1 | 3/2004 | |
| WO | 2013/003397 A2 | 1/2013 | |
| WO | WO 2013048069 A1 * | 4/2013 | G03F 7/0233 |

OTHER PUBLICATIONS

First Chinese Office Action dated Jul. 20, 2015, Appln. No. 201410367033.X.
International Search Report & Written Opinion Appln. No. PCT/CN2014/091835; dated May 6, 2015.

(56) References Cited

OTHER PUBLICATIONS

Extended European Search Report dated Mar. 14, 2018; Appln. No. 14882151.5.
Yong Fan, et al; "Synthesis and Characterization of Polymide Alumina Nano-hybrid Film", Insulating Materials, Feb. 2007, 4 pages.
Yoshikazu Nishida, et al; "Surface modification of silica particles with polyimide by ultrasonic wave irradiation", VSP and Society of Powder Technology, Japan 2005, Also available online—www.vsppub.com, Japan 2005, 10 pages.
The First Chinese Office Action dated Jul. 14, 2015; Appln. No. 201410367829.5.
The First Chinese Office Action dated Jul. 28, 2015; Appln. No. 201410366432.4.
The International Search Report and Written Opinion dated May 4, 2015; PCT/CN2014/091859.
The Extended European Search Report dated Jan. 30, 2018; Appln. No. 14882143.2.
The Extended European Search Report dated Feb. 22, 2018; Appln. No. 14861170.0.
The Extended European Search Report dated Apr. 6, 2018; Appln. No. 14882799.1.
USPTO NFOA dated Aug. 30, 2016 in connection with U.S. Appl. No. 14/646,099.
USPTO NFOA dated Oct. 14, 2016 in connection with U.S. Appl. No. 14/771,040.
USPTO NFOA dated Oct. 25, 2016 in connection with U.S. Appl. No. 14/769,586.
USPTO NFOA dated Feb. 14, 2017 in connection with U.S. Appl. No. 14/646,099.
USPTO NFOA dated Jun. 21, 2017 in connection with U.S. Appl. No. 14/646,099.
USPTO NFOA dated Dec. 5, 2017 in connection with U.S. Appl. No. 14/770,935.

\* cited by examiner

FUNCTIONAL MATERIAL, ITS PREPARATION METHOD, AND ORGANIC LIGHT EMITTING DIODE DISPLAY PANEL

TECHNICAL FIELD

The present invention relates to the display technical field, in particular to a functional material, its preparation method, and an organic light emitting diode display panel.

BACKGROUND

Organic light emitting diode (OLED) display panels are more and more extensively used in computers, televisions, mobile phones and the like.

However, organic light emitting diode display panels will inevitably produce some electromagnetic radiation pollution, which will affect human health. In particular, the radiation pollution produced by mobile phones exerts a more notable impact on a human body since they are generally used very close to a human body.

SUMMARY OF THE INVENTION

Regarding the problem that current organic light emitting diode display panels will produce pollution, the present invention provides an environmentally friendly functional material which can play a role in heath care and a method for preparing the same, as well as an organic light emitting diode display panel.

One technical solution employed to address a technical problem of the present invention is a functional material comprising an inorganic mixed powder whose surface has a modified layer, wherein the inorganic mixed powder comprises a primary ingredient and a secondary ingredient;
the primary ingredient consisting of boron oxide, sodium oxide, lithium oxide, and zirconium oxide;
the secondary ingredient including any one or more of aluminum oxide, zinc oxide, titanium dioxide, silicon dioxide, calcium oxide, silver complexes, silver phosphate, silver nitrate, tourmaline, silver thiosulfate, carbon nanotubes, aluminum sulfate, manganese, manganese oxide, iron, iron oxide, cobalt, cobalt oxide, nickel, nickel oxide, chromium, chromium oxide, copper, copper oxide, magnesium oxide, boron carbide, silicon carbide, titanium carbide, zirconium carbide, tantalum carbide, molybdenum carbide, boron nitride, chromium nitride, titanium nitride, zirconium nitride, aluminum nitride, chromium boride, $Cr_3B_4$, titanium boride, zirconium boride, tungsten disilicide, and titanium disilicide; and the modified layer being generated by a reaction of a dianhydride and a diamine.

For example, the molar ratio of the dianhydride to the diamine for generating the modified layer is between 0.85:1 and 1.05:1.

More preferably, the molar ratio of the dianhydride to the diamine for generating the modified layer is between 0.92:1 and 1.05:1.

For example, the dianhydride for generating the modified layer comprises at least one phenyl group, and the diamine for generating the modified layer comprises at least one phenyl ring or at least one non-phenyl six-membered carbocyclic ring.

More preferably, the dianhydride for generating the modified layer is selected from any one of pyromellitic dianhydride, trimellitic anhydride, benzophenone dianhydride, biphenyl dianhydride, diphenyl ether dianhydride, and 4,4'-(hexafluoroisopropylidene) diphthalic anhydride; the diamine for generating the modified layer is selected from any one of 3-amino-benzylamine, 2,2'-difluoro-4,4'-(9-fluorenylidene) dianiline, 2,2-bis(3-amino-4-hydroxyphenyl) hexafluoropropane, hexahydro-m-xylylene diamine, 1,4-bis (aminomethyl)cyclohexane, 2,2-bis[4-(4-aminophenoxy) phenyl] hexafluoropropane, 2,2-bis(3-amino-4-methylphenyl) hexafluoropropane, 2,2-bis(3-aminophenyl) hexafluoropropane, 2,2-bis(4-aminophenyl) hexafluoropropane, 2,7-diamino-fluorene, m-xylylene diamine, and 4,4'-methylene bis(2-ethyl-6-methylaniline).

For example, the inorganic mixed powder has a particle diameter of 1 to 5000 nm.

One technical solution employed to solve a technical problem of the present invention is a method for preparing the above functional material, comprising: mixing the inorganic mixed powder, the dianhydride, and the diamine with an initiator and a solvent uniformly; and
reacting the dianhydride with the diamine by heating to form the modified layer on the surface of the inorganic mixed powder.

For example, the mass ratio of the inorganic mixed powder to the substance generated by the reaction of the dianhydride and the diamine is between 20:1 and 1:1.

More preferably, the initiator is any one of azo bisisobutyronitrile, 2,2'-azo-bis-(2,4-dimethylvaleronitrile), dimethyl azobisisobutyrate and azo bisisovaleronitrile.

For example, the heating comprises two steps: heating at a temperature of 35 to 70° C. for 20 to 40 min; and heating at a temperature of 70 to 100° C. for 20 to 40 min.

One technical solution employed to solve a technical problem of the present invention is an organic light emitting diode display panel comprising an organic light emitting diode and an encapsulation structure for encapsulating the organic light emitting diode, wherein the surface and/or interior of the encapsulation structure comprise(s) the above functional material.

For example, the interior of the encapsulation structure comprises the functional material in an amount of 0.1 to 30% by mass; and/or, the surface of the encapsulation structure has a surface film layer with a thickness of 50 to 1000 nm which comprises the functional material in an amount of 0.1 to 10% by mass.

More preferably, the interior of the encapsulation structure comprises the functional material in an amount of 3 to 20% by mass; and/or, the surface film layer comprises the functional material in an amount of 0.5 to 5% by mass.

Functional materials of the present invention can emit far-infrared light and negative ions. Far-infrared light, after being absorbed by a human body, can allow water molecules in the body to resonate and be activated, which enhances the intermolecular bonding force, thereby activating proteins and other biological macromolecules and bringing the organism cells to the highest vibration level. Furthermore, far-infrared heat can be transferred to a subcutaneous deeper part, thus increasing the temperature of the subcutaneous deeper part, expanding the capillaries, promoting the blood circulation, strengthening the metabolism among tissues, promoting a tissue regeneration capacity, enhancing the organism immunity, and bringing the vivacity. On the other hand, negative ions can decompose and oxidize bacteria and organic substances, and may serve the function of disinfection and sterilization and produce the effect of improving air quality. Therefore, the functional material may play a role in health care and is environmentally friendly.

The surface of the inorganic mixed powder in the functional material according to the present invention has a modified layer, which can allow the inorganic mixed powder to bond well with the encapsulation structure and can further improve the inorganic mixed powder's capacity to emit far-infrared light and negative ions, so that the functional material is well incorporated into the organic light emitting diode display panel to increase its environmental friendliness without affecting the performance of the organic light emitting diode display panel itself.

DETAILED DESCRIPTION

Figure 1:
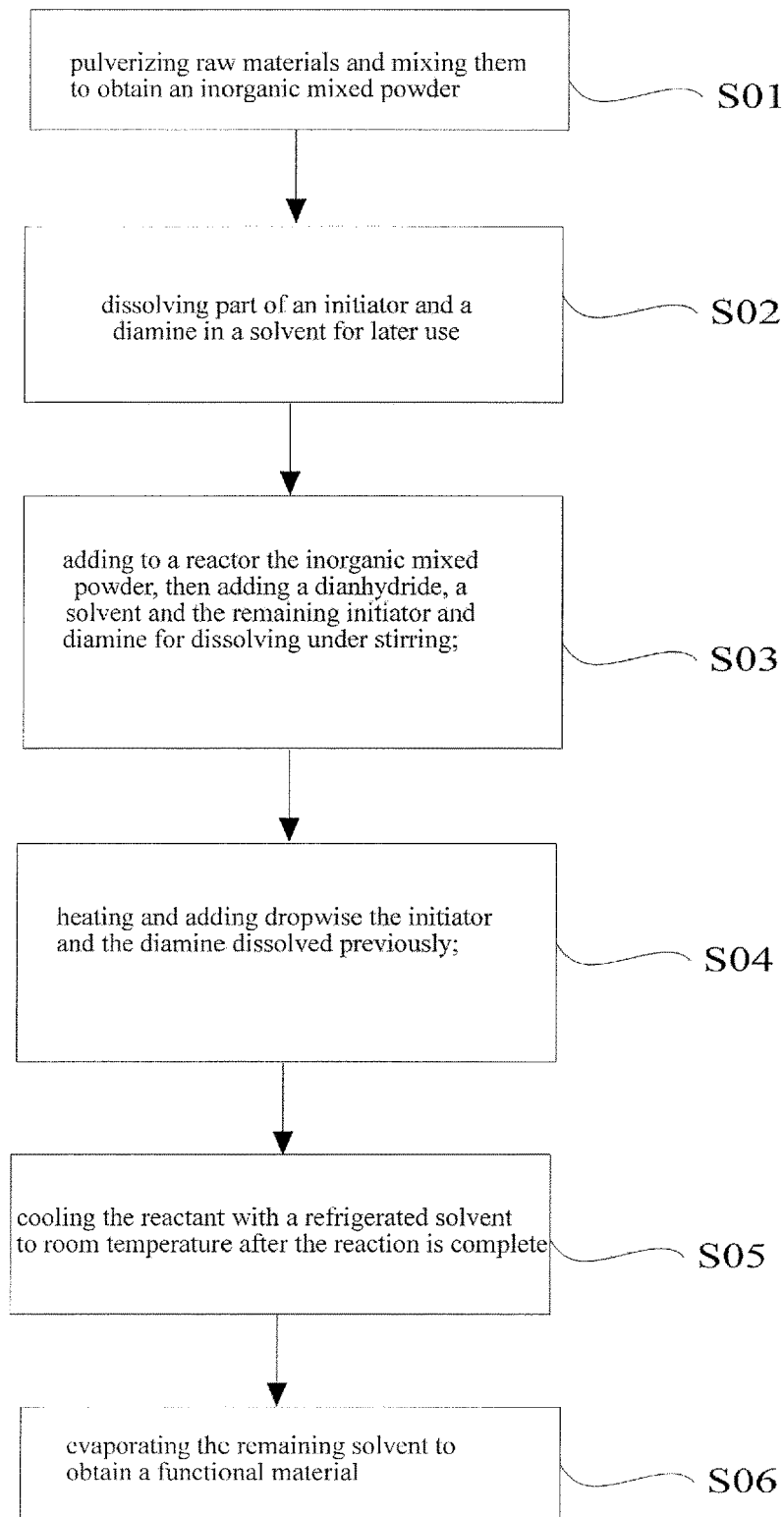
FIG. 1 is a flow chart of a method for preparing a functional material according to an embodiment of the present invention.

To enable those skilled in the art to better understand the technical solution of the present invention, further detailed descriptions are made for the present invention with reference to the drawings and embodiments.

The present embodiment provides a functional material and a method for preparing the same.

The functional material comprises an inorganic mixed powder having a modified layer on its surface, wherein the inorganic mixed powder comprises a primary ingredient and a secondary ingredient;
the primary ingredient consisting of boron oxide, sodium oxide, lithium oxide, and zirconium oxide;
the secondary ingredient including any one or more of aluminum oxide, zinc oxide, titanium oxide, silicon dioxide, calcium oxide, silver complexes, silver phosphate, silver nitrate, tourmaline, silver thiosulfate, carbon nanotubes, aluminum sulfate, manganese, manganese oxide, iron, iron oxide, cobalt, cobalt oxide, nickel, nickel oxide, chromium, chromium oxide, copper, copper oxide, magnesium oxide, boron carbide, silicon carbide, titanium carbide, zirconium carbide, tantalum carbide, molybdenum carbide, boron nitride, chromium nitride, titanium nitride, zirconium nitride, aluminum nitride, chromium boride, $Cr_3B_4$, titanium boride, zirconium boride, tungsten disilicide, and titanium disilicide; and the modified layer being generated by reaction of a dianhydride and a diamine.

The particle diameter of the inorganic mixed powder is from nanometers to micrometers, specifically, for example, from 1 to 5000 nm, preferably from 10 to 500 nm. The particle diameter can be measured, for example by a Malvern laser particle size analyzer.

Dianhydride refers to a substance containing at least two anhydride groups in the molecular structure; while diamine refers to a substance containing at least two amine groups (or amino groups) in the molecular structure.

The dianhydride, for example, contains at least one phenyl group, and is preferably any one of pyromellitic dianhydride, trimellitic anhydride, benzophenone dianhydride, biphenyl dianhydride, diphenyl ether dianhydride, and 4,4'-(Hexafluoroisopropylidene)diphthalic anhydride.

The diamine, for example, contains at least one phenyl ring or at least one non-phenyl six-membered carbocyclic ring (e.g. cyclohexane), and is preferably any one of 3-amino-benzylamine, 2,2'-difluoro-4,4'-(9-fluorenylidene) dianiline, 2,2-bis(3-amino-4-hydroxyphenyl) hexafluoropropane, hexahydro-m-xylylene diamine, 1,4-bis(aminomethyl) cyclohexane, 2,2-bis[4-(4-aminophenoxy)phenyl] hexafluoropropane, 2,2-bis(3-amino-4-methylphenyl) hexafluoropropane, 2,2-bis(3-aminophenyl) hexafluoropropane, 2,2-bis(4-aminophenyl) hexafluoropropane, 2,7-diamino-fluorene, m-xylylene diamine, and 4,4'-methylene bis(2-ethyl-6-methylaniline).

The molar ratio of the dianhydride to the diamine is from 0.85:1 to 1.05:1, preferably from 0.92:1 to 1.05:1.

Our studies have revealed that the modified layer generated by reaction of the above dianhydride and diamine can desirably improve the properties of the inorganic mixed powder.

Functional materials of the present embodiment can emit far-infrared light and negative ions. Far-infrared light, after being absorbed by a human body, can allow water molecules in the body to resonate and be activated, which enhances the intermolecular bonding force, thereby activating proteins and other biological macromolecules and bringing the organism cells to the highest vibration level. Furthermore, far-infrared heat can be transferred to a subcutaneous deeper part, thus increasing the temperature of the subcutaneous deeper part, expanding the capillaries, promoting the blood circulation, strengthening the metabolism among tissues, promoting a tissue regeneration capacity, enhancing the organism immunity, and bringing the vivacity. On the other hand, negative ions can decompose and oxidize bacteria and organic substances, and may serve the function of disinfection and sterilization and produce the effect of improving air quality. Therefore, the functional material may play a role in health care and is environmentally friendly.

The method for preparing the above functional material comprises: mixing the inorganic mixed powder, the dianhydride, and the diamine with an initiator and a solvent uniformly; and reacting the dianhydride with the diamine by heating to form the modified layer on the surface of the inorganic mixed powder.

To be specific, as shown in FIG. 1, the above preparation method may comprise:

S01 in the case of using a dispersant, pulverizing the raw materials respectively into powder and mixing the same uniformly in proportion, or mixing the raw materials in proportion uniformly and then pulverizing the same, to yield an inorganic mixed powder.

The dispersant may be chosen from conventional dispersants such as BYK 161 manufactured by BYK Additives & Instruments and Solsperse 32500 and Solsperse 22000 manufactured by The Lubrizol Corporation. Pulverization may be carried out using conventional methods such as ball milling, grinding, and the like. As the inorganic mixed powder may be prepared by existing methods, no further details will be provided herein.

S02, dissolving from a fourth to a third of an initiator and from a fourth to a third of a diamine in a solvent for later use.

The mass ratio of the inorganic mixed powder to the substance generated by the reaction of the dianhydride and the diamine is from 20:1 to 1:1.

That is to say, the amounts of the dianhydride and the diamine are determined as follows: assuming a complete reaction between the dianhydride and the diamine to yield a resultant (which is actually a modified layer), if the mass of the resultant is 1, then the mass of the inorganic mixed powder is between 1 and 20. Such an amount can ensure that a modifier layer with a suitable thickness can be obtained on the inorganic mixed powder.

An initiator is used to initiate the reaction, which, for example, is a nitrogen-based initiator, preferably any one of azo bisisobutyronitrile, 2,2'-azo bis(2,4-dimethylvaleronitrile), dimethyl azo bisisobutyrate, and azo bisisovaleronitrile.

The solvent can be selected from fatty alcohols, glycol ethers, ethyl acetate, methyl ethyl ketone, methyl isobutyl ketone, ethylene glycol monomethyl ether, γ-butyrolactone, ethyl 3-ethoxypropionate, butyl carbitol, butyl carbitol acetate, propylene glycol monomethyl ether, propylene glycol monomethyl ether acetate, cyclohexane, xylene, isopropanol, and other conventional organic solvents. Since the choice of the solvent has no significant effect on the performance of the final product, propylene glycol monomethyl ether acetate is used in all the Examples as the solvent.

S03, adding the inorganic mixed powder to a reaction vessel (e.g., a four-neck flask) which is then subjected to stirring, shocking, shaking and the like; afterwards, adding the dianhydride and the solvent as well as the remaining initiator and diamine and allowing them to be dissolved uniformly.

S04, heating to carry out the reaction for example in two steps, specifically comprising: heating at a temperature of 35 to 70° C. for 20 to 40 min; and then continuing heating at a temperature of 70 to 100° C. for 20 to 40 min.

During the above heating process, the dianhydride and the diamine are allowed to react, thereby generating a modified layer on the surface of the inorganic mixed powder; wherein heating is carried out in two steps so as to prevent the reaction from being too severe.

During the reaction process, the above solution prepared by dissolving an initiator and a diamine is gradually added dropwise to a four-neck flask so as to prevent the reaction from being too severe.

The reaction in this step may be carried out, for example, under the protection of nitrogen, and for example under constant stirring.

The solvent in each step is in an amount sufficient to disperse and dissolve the substances therein uniformly, while the initiator is in an amount sufficient to initiate the reaction, which can be adjusted by those skilled in the art based on the actual conditions, and thus no further detail is given herein. However, the mass ratio (all referring to the total amount) of the inorganic mixed powder, the initiator and the solvent is generally 1:(from 0.25 to 0.4):(from 1 to 1.5). To achieve consistency in the process of preparing the functional material in the various Examples, the mass ratio of the inorganic powder, the initiator and the solvent is 1:0.3:1.4.

S05, cooling the reactant with a refrigerated solvent to room temperature (at about 10 to 30° C.) after the reaction is complete.

S06, evaporating the remaining solvent or separating the powder therefrom, to yield an inorganic mixed powder with a modified layer, i.e., a functional material.

Of course, it should be appreciated that the preparation method described above may undergo a number of variations, e.g., the dianhydride, the diamine, and the initiator can be dissolved once in the solvent; for another example, heating can be carried out in one step. After all, any variation is allowed as long as the dianhydride and the diamine can react to form a modified layer on the surface of the inorganic mixed powder.

The infrared emissivity of the functional material is measured according to the GB/T 7287-2008 standard test, and the amount of anions generated by the functional material is measured using an air anion analyzer (for example, Japan KEC Corporation's KEC-900 type).

Various functional materials were prepared according to the method described above, where the materials, amounts, parameters and product properties are shown in the following tables.

TABLE 1

Information about the primary ingredient in the inorganic mixed powder of the functional materials in Examples (content unit: by mass parts)

| Example # | Content of Boron Oxide | Content of Sodium Oxide | Content of Lithium Oxide | Content of Zirconium Oxide |
|---|---|---|---|---|
| 1 | 3.83 | 1.83 | 6.73 | 20 |
| 2 | 5.18 | 2.27 | 8.16 | 25 |
| 3 | 6.5 | 3.6 | 10.5 | 30 |
| 4 | 7.17 | 3.6 | 10.5 | 30 |

TABLE 2

Information about the secondary ingredient in the inorganic mixed powder of the functional materials in Examples (content unit: by mass parts)

| Example # | Secondary Ingredient 1 Type | Secondary Ingredient 1 Content | Secondary Ingredient 2 Type | Secondary Ingredient 2 Content | Secondary Ingredient 3 Type | Secondary Ingredient 3 Content |
|---|---|---|---|---|---|---|
| 1 | Silicon Dioxide | 40 | Manganese Oxide | 1.2 | Calcium Oxide | 0.98 |
| 2 | Silicon Dioxide | 40 | Aluminum Nitride | 15 | Silver Phosphate | 3 |
| 3 | Silicon Dioxide | 40 | Nickel Oxide | 1.4 | Chromic Oxide | 1.4 |
| 4 | Alumina | 10 | Magnesium Oxide | 10 | None | None |

TABLE 3

Information about raw materials for preparing a modified layer in the functional materials of Examples

| Example # | Dianhydride Type | Diamine Type | Mass Ratio of Dianhydride to Diamine | Mass Ratio of Inorganic Mixed Powder to Resultant | Initiator Type |
|---|---|---|---|---|---|
| 1 | Benzophenone Dianhydride | 1,4-bis (aminomethyl) cyclohexane | 0.85:1 | 20:1 | Azobisisovaleronitrile |
| 2 | Biphenyl Dianhydride | 3-amino-benzylamine | 0.92:1 | 1:1 | Azobisisovaleronitrile |
| 3 | 4,4'-(Hexafluoro-isopropylidene)diphthalic anhydride | Hexahydro-m-xylylene diamine | 1:1 | 12:1 | Azobisisobutyronitrile |
| 4 | Pyromellitic Dianhydride | 2,7-diamino-fluorene | 1.05:1 | 15:1 | 2,2'-azobis(2,4-dimethylvaleronitrile) |

TABLE 4

Preparation parameters and performance testing results of the functional materials in Examples

| Example # | Heating temperature at the first stage (° C.) | Heating duration at the first stage (min) | Heating temperature at the second stage (° C.) | Heating duration at the second stage (min) | Infrared emissivity (%) | Anion concentration (per cubic centimeter) |
|---|---|---|---|---|---|---|
| 1 | 35 | 40 | 70 | 40 | 85 | 2572 |
| 2 | 70 | 20 | 100 | 20 | 88 | 2466 |
| 3 | 45 | 35 | 80 | 35 | 92 | 2785 |
| 4 | 55 | 25 | 90 | 25 | 94 | 2810 |

As can be seen from the above, all the functional materials of the Examples have a high infrared emissivity and a high anion concentration, which indicates that they actually can produce far-infrared light and anions, thereby improving the environment.

The present embodiment further provides an organic light emitting diode display panel comprising an organic light emitting diode and an encapsulation structure for encapsulation the organic light emitting diode, wherein the surface and/or interior of the encapsulation structure comprise(s) the above functional material.

Figure 2:
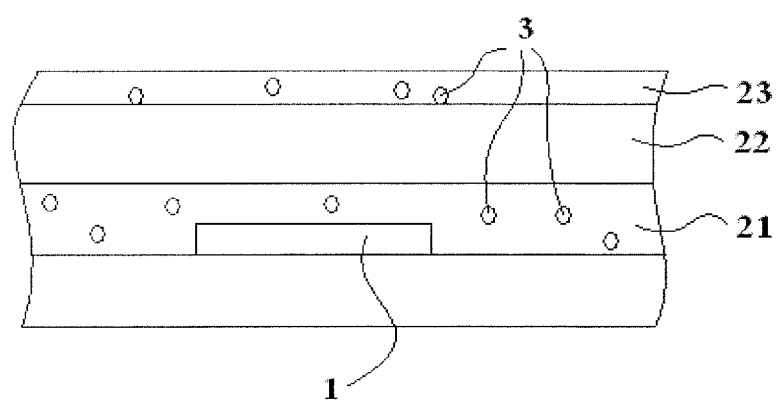
FIG. 2 is a partial schematic cross-sectional structure of the organic light emitting diode display panel according to an embodiment of the present invention;
wherein the reference signs are:
1. an organic light emitting diode; 21. an encapsulation layer; 22. an encapsulation substrate; 23. a surface film layer; and 3 a functional material.

As shown in FIG. 2, the most primary structure of the organic light emitting diode display panel is a plurality of organic light emitting diodes 1 (which can be provided in an array substrate). However, since the light emitting layer in the organic light emitting diode 1 tends to be affected by water, oxygen and the like, it generally needs to be encapsulated using an encapsulation structure so as to be isolated from the outside environment.

Specifically, the encapsulation structure may comprise an encapsulation layer 21 and an encapsulation substrate 22; wherein the encapsulation substrate 22 is typically a glass plate and is assembled with an array substrate in which the organic light emitting diode 1 is located, thereby encapsulating the organic light emitting diode 1 therein.

However, the encapsulation layer 21 is a layer structure provided on the organic light emitting diode 1 or around the organic light emitting diode 1. According to the difference in the display panel structure, the encapsulation layer may comprise one or more of a sealing layer, an insulating layer (e.g., silicon nitride layer), a getter, a binding layer and the like. As the specific forms of the encapsulation layer 21 are known and diverse, it will not be further described in detail.

For example, the mass percentage of the functional material in the encapsulation structure is 0.1 to 30%; and/or, the surface of the encapsulation structure has a surface film layer with a thickness of 50 to 1000 nm which comprises the functional material in an amount of 0.1 to 10% by mass.

In other words, the interior of the encapsulation substrate 22 and/or encapsulation layer 21 may comprise the functional material 3 and its mass percentage (based on the total mass 100% of the encapsulation structure and the functional material 3) is, for example, 0.1 to 30%, preferably 3 to 20%. Specifically, the functional material 3 can be added to the materials (for example, getters, binders and the like) for forming an encapsulation structure so that the functional material 3 is naturally formed therein upon forming an encapsulation structure from the above materials by means of coating and the like. Alternatively, an encapsulating layer 21 such as all insulating layer, a sealing layer and the like is formed by means of chemical vapor deposition (CVD) and the like, and then the functional material 3 is incorporated therein by means of sputtering and the like.

Alternatively, a surface film layer 23 having a thickness of 50 to 1000 nm can be provided on the surface of the encapsulation substrate 22 and/or encapsulation layer 21, and the above functional material 3 is distributed in the surface film layer 23 in an amount of, for example, 0.1 to 10% by mass, preferably 0.5 to 5% by mass. Specifically, the functional material 3 can be dispersed in a solvent to form a suspension which is then applied to the surface of the encapsulation structure by means of coating, spraying and the like. After curing, a surface film layer 23 is formed.

By observing the organic light emitting diode display panel to which the functional material 3 has been added, it was found out that the functional material 3 therein does not involve any phenomenon such as agglomeration, shedding, etc., which suggests that the functional material 3 of the present embodiment can be well bonded to the organic light emitting diode display panel and will not produce adverse effects on the properties thereof.

The surface of the inorganic mixed powder in the functional material 3 of the present embodiment has a modified layer which can allow the inorganic mixed powder to bond well to an encapsulation structure and can improve the ability of the inorganic mixed powder to emit far-infrared rays and negative ions, so that the functional material 3 can be well incorporated into the organic light emitting diode display panel to increase its environmental friendliness without affecting the performance of the organic light emitting diode display panel itself.

The organic light emitting diode display panel of the present embodiment is particularly suitable for being used in mobile phones.

It should be appreciated that the above embodiments are merely exemplary embodiments to illustrate the principles of the present invention, but the present invention is not limited thereto. Those of ordinary skill in the art, without departing from the spirit and essence of the present invention, may make various changes and improvements. Such changes and improvements are deemed within the scope of the invention.

The present application claims the priority of the Chinese Patent Application No. 201410367033.X filed on Jul. 29, 2014, which is incorporated herein by reference as part of the present application.

What is claimed is:

1. An organic light emitting diode display panel comprising an organic light emitting diode and an encapsulation structure for encapsulating the organic light emitting diode, wherein the surface and/or interior of the encapsulation structure comprise(s) a functional material consisting of an inorganic mixed powder and a modified layer on the surface of the inorganic mixed powder, wherein the inorganic mixed powder comprises boron oxide, sodium oxide, lithium oxide, zirconium oxide and any one or more of aluminum oxide, zinc oxide, titanium dioxide, silicon dioxide, calcium oxide, silver complexes, silver phosphate, silver nitrate, tourmaline, silver thiosulfate, carbon nanotubes, aluminum sulfate, manganese, manganese oxide, iron, iron oxide, cobalt, cobalt oxide, nickel, nickel oxide, chromium, chromium oxide, copper, copper oxide, magnesium oxide, boron carbide, silicon carbide, titanium carbide, zirconium carbide, tantalum carbide, molybdenum carbide, boron nitride, chromium nitride, titanium nitride, zirconium nitride, aluminum nitride, chromium boride, $Cr_3B_4$, titanium boride, zirconium boride, tungsten disilicide, and titanium disilicide; and the modified layer is generated by a reaction of only one dianhydride and only one diamine, wherein the dianhydride for generating the modified layer is selected from the group consisting of pyromellitic dianhydride, benzophenone dianhydride, biphenyl dianhydride, diphenyl ether dianhydride, and 4,4'-(hexafluoroisopropylidene)diphthalic anhydride; and the diamine for generating the modified layer is selected from the group consisting of 3-aminobenzylamine, 2,2'-difluoro-4,4'-(9-fluorenylidene) dianiline, 2,2-bis(3-amino-4-hydroxyphenyl) hexafluoropropane, hexahydro-m-xylylene diamine, 1,4-bis(aminomethyl)cyclohexane, 2,2-bis[4-(4-amino phenoxy)phenyl] hexafluoropropane, 2,2-bis(3-amino-4-methylphenyl) hexafluoropropane, 2,2-bis(3-aminophenyl) hexafluoropropane, 2,2-bis(4-aminophenyl) hexafluoropropane, 2,7-diaminofluorene, m-xylylene diamine, and 4,4'-methylene bis(2-ethyl-6-methylaniline), wherein the interior of the encapsulation structure comprises the functional material in an amount of 0.1 to 30% by mass; and/or the surface of the encapsulation structure has a surface film layer with a thickness of 50 to 1000 nm which comprises the functional material in an amount of 0.1 to 10% by mass.

2. The organic light emitting diode display panel according to claim 1, wherein the interior of the encapsulation structure comprises the functional material in an amount of 3 to 20% by mass; and/or the surface film layer comprises the functional material in an amount of 0.5 to 5% by mass.

3. The organic light emitting diode display panel according to claim 1, wherein the molar ratio of the dianhydride to the diamine for generating the modified layer is between 0.85:1 and 1.05:1.

4. The organic light emitting diode display panel according to claim 3, wherein the molar ratio of the dianhydride to the diamine for generating the modified layer is between 0.92:1 and 1.05:1.

5. The organic light emitting diode display panel according to claim 4, wherein the inorganic mixed powder has a particle diameter of 1 to 5000 nm.

6. The organic light emitting diode display panel according to claim 3, wherein the inorganic mixed powder has a particle diameter of 1 to 5000 nm.

7. The organic light emitting diode display panel according to claim 1, wherein the inorganic mixed powder has a particle diameter of 1 to 5000 nm.

* * * * *